(12) United States Patent
Zuckerman-Stark et al.

(10) Patent No.: US 12,369,851 B2
(45) Date of Patent: Jul. 29, 2025

(54) DEVICE, SYSTEM AND METHOD FOR PERIOPERATIVE PAIN MANAGEMENT (71) Applicant: Medasense Biometrics Ltd., Ramat Gan (IL)

(72) Inventors: Galit Zuckerman-Stark, Tel Aviv (IL); Adi Costa, Kfar Saba (IL)

(73) Assignee: MEDASENSE BIOMETRICS LTD., Ramat Gan (IL)

( * ) Notice: Subject to any disclaimer, the term of this patent is extended or adjusted under 35 U.S.C. 154(b) by 777 days.

(21) Appl. No.: 17/609,390

(22) PCT Filed: May 19, 2020

(86) PCT No.: PCT/IL2020/050549
§ 371 (c)(1),
(2) Date: Nov. 7, 2021

(87) PCT Pub. No.: WO2020/234877
PCT Pub. Date: Nov. 26, 2020

(65) Prior Publication Data
US 2022/0233139 A1 Jul. 28, 2022

Related U.S. Application Data (60) Provisional application No. 62/850,392, filed on May 20, 2019.

(51) Int. Cl.
*A61B 5/00* (2006.01)
*A61B 5/0205* (2006.01)
(Continued)

(52) U.S. Cl.
CPC .......... *A61B 5/4821* (2013.01); *A61B 5/4839* (2013.01); *A61B 5/7264* (2013.01);
(Continued)

(58) Field of Classification Search
CPC ................ A61B 5/4821; A61B 5/4824; A61B 5/4839; A61B 5/7264; A61M 5/1723; G16H 20/13; G16H 20/17; G16H 50/20; G16H 50/30
See application file for complete search history.

(56) References Cited

U.S. PATENT DOCUMENTS

| 2003/0055355 A1 | 3/2003 | Viertio-Oja |
| 2005/0010116 A1 | 1/2005 | Korhonen et al. |

(Continued)

FOREIGN PATENT DOCUMENTS

| EP | 1704818 | 9/2006 |
| EP | 1742155 | 10/2007 |

(Continued)

OTHER PUBLICATIONS

Anatomy and Physiology of Pain, http://www.nursingtimes.net/clinical-archives/pain-management/anatomy-and-physiology-of-pain-18-09-2008/.

(Continued)

*Primary Examiner* — Nathan R Price
*Assistant Examiner* — Haden Matthew Ritchie
(74) *Attorney, Agent, or Firm* — Greenberg Traurig, LLP (57) ABSTRACT Method, device, system and associated processing logic for providing optimal perioperative nociception management to anesthetized patient, including monitoring a plurality of nociception-related physiological parameters of the patient using at least two non-invasive physiological sensors; combining the plurality of nociception-related physiological parameters into a nociception index value indicative of a level of nociception of the patient, by applying a machine learning algorithm on the plurality of nociception-related physiological parameters and/or features derived therefrom; comparing the nociception index value to a first threshold (Continued)

value indicative of an upper limit of nociceptive-anti-nociceptive balance (NANB) and to a second threshold value indicative of a lower limit of NANB; and providing a treatment or treatment recommendation based on the comparison and on a clinical concern.

11 Claims, 3 Drawing Sheets

(51) Int. Cl.
| | |
|---|---|
| *G16H 20/13* | (2018.01) |
| *G16H 20/17* | (2018.01) |
| *G16H 50/20* | (2018.01) |
| *G16H 50/30* | (2018.01) |
| *A61M 5/172* | (2006.01) |

(52) U.S. Cl.
CPC ............ *G16H 20/13* (2018.01); *G16H 20/17* (2018.01); *G16H 50/20* (2018.01); *G16H 50/30* (2018.01); *A61M 5/1723* (2013.01)

(56) References Cited

U.S. PATENT DOCUMENTS

| | | | |
|---|---|---|---|
| 2006/0004296 | A1 | 1/2006 | Huiku et al. |
| 2006/0217614 | A1 | 9/2006 | Takala et al. |
| 2007/0282251 | A1 | 12/2007 | Barvais et al. |
| 2008/0242955 | A1 | 10/2008 | Uutela et al. |
| 2010/0249543 | A1 | 9/2010 | Sethi et al. |
| 2011/0245633 | A1 | 10/2011 | Goldberg et al. |
| 2013/0310660 | A1 | 11/2013 | Zukerman-Stark et al. |
| 2014/0276549 | A1 | 9/2014 | Osorio |
| 2015/0025334 | A1 | 1/2015 | Jain |
| 2018/0000409 | A1 | 1/2018 | Jensen et al. |
| 2018/0085055 | A1 | 3/2018 | Annoni et al. |
| 2018/0310877 | A1* | 11/2018 | Zuckerman Stark .. A61B 5/392 |

FOREIGN PATENT DOCUMENTS

| | | | |
|---|---|---|---|
| WO | 2008043364 | A1 | 4/2008 |
| WO | 2014169060 | A1 | 10/2014 |

OTHER PUBLICATIONS

Sabourdin et al (2012) Pain monitoring in anesthetized children: first assessment of skin conductance and analgesia-nociception index at different infusion rates of remifentanil, Pediatric Anesthesia, 23 (149-155). doi:10.1111/pan.12071.

Cowen, et al, (2015) "Assessing pain objectively: the use of physiological markers", Anesthesia, pp. 1-20. doi:10.1111/anae.13018.

Schnackers et al (2009). The Nociception Coma Scale: A New Tool to Assesss Nociception in Disorders of Consciousness. Pain, vol. 148, No. 2, pp. 215-219, Oct. 24, 2009. doi:10.1016/j.pain.2009.09.028.

Aran et al. (1990). Antinociception produced by interactions between intrathecally administered adenosine agonists and norepiniephrine. Brain Research, vol. 513, No. 2, pp. 255-263, Apr. 16, 1990.

Santonocito et al (2018) Remifentanil-induced postoperative hyperalgesia: current perspectives on mechanisms and therapeutic strategies,Local Reg Anesth, pp. 15-23. http://dx.doi.org/10.2147/LRA.S143618.

Chen et al (2015) Cardiac Effects of Opioid Therapy, Pain Medicine, 16: S27-S31. DOI: 10.1111/pme.12915.

Levitan et al (2011) The complexities of tracheal intubation with direct laryngoscopy and alternative intubation devices, Ann Emerg Med., 57(3):240-247. doi:10.1016/j.annemergmed.2010.05.035.

Meijer et al (2019) Nociception-guided versus Standard Care during Remifentanil-Propofol Anesthesia: A Randomized Controlled Trial, Anesthesiology, 130(5):745-755. doi: 10.1097/ALN.0000000000002634.

Edry et al (2016) Preliminary intraoperative validation of the Nociception Level Index, a noninvasive nociception monitor, Anesthesiology 125: 193-203. doi: 10.1097/ALN.0000000000001130.

Martini et al (2015) Ability of the Nociception Level, a multiparameter composite of autonomic signals, to detect noxious stimuli during propofol-remifentanil anesthesia, Anesthesiology 123:524-34. doi: 10.1097/ALN.0000000000000757.

Maheshwari et al (2017) Prolonged concurrent hypotension and low bispectral index ("double low" are associated with mortality, serious complications, and prolonged hospitalization after cardiac surgery, Br J Anaesth 119(1):40-49. doi: 10.1093/bja/aex095.

Bollag et al (2018) The nociception level index (NOL) response to intubation and incision in patients undergoing video-assisted thoracoscopic surgery (VATS) with and without thoracic epidural analgesia. A pilot study, F1000Research 7:875L. doi: 10.12688/f1000research.15279.1.

Fleur et al (2019) Nociception-guided versus Standard Care during Remifentanil-Propofol Anesthesia, A Randomized Controlled Trial, Anesthesiology 130. doi: 10.1097/ALN.0000000000002634.

Speghen et al (2018) Nol Index Response After Laryngoscopy Performed With Macintosh Blade Version GlidescopeTm Videolaryngoscope, ASA18Abstract (http://www.asaabstracts.com/strands/asaabstracts/abstract.htm?year=2018&index=7&absnum=3533).

PCT International Search Report for International Application No. PCT/IL2016/050714, mailed Jan. 25, 2017, 2pp.

PCT Written Opinion for International Application No. PCT/IL2016/050714, mailed Jan. 25, 2017, 8pp.

PCT International Search Report for International Application No. PCT/IL2020/050549, mailed Sep. 3, 2020, 2pp.

PCT Written Opinion for International Application No. PCT/IL2020/050549, mailed Sep. 3, 2020, 5pp.

Korhonen et al (2009) Photoplethysmography and nociception, Acta Anaesthesiologica Scandinavica, 5:975-985.

Jeanne et al (2009) Heart rate variability during total intravenous anesthesia: Effects of nociciption and anesthesia, Autonomic Neuroscience: Basic and Clinical, 147:91-96.

Hans et al (2012) Effect of a fluid challenge on the Surgical Pleth Index during stable propofol-remifentanil anesthesia, Acta Anesthesiologica Scandinavica, 6:787-796.

\* cited by examiner

DEVICE, SYSTEM AND METHOD FOR PERIOPERATIVE PAIN MANAGEMENT

CROSS REFERENCE TO RELATED APPLICATIONS

This application is a National Phase of PCT Patent Application No. PCT/IL2020/050549 having International filing date of May 19, 2020, which claims the benefit of priority of U.S. Provisional Patent Application No. 62/850,392, filed May 20, 2019, the contents of which are all incorporated herein by reference in their entirety.

TECHNICAL FIELD

The present disclosure generally relates to the field of perioperative or critical care pain management, specifically to pain management during anesthesia and specifically to providing automatic pain management (close loop) or semi-automatic pain management (open loop).

BACKGROUND

The role of anesthesia is to provide optimal conditions for surgeons/interventionists to treat patients whilst ensuring patient safety and comfort. To achieve this goal during general anesthesia; hypnosis, analgesia (best termed anti-nociception during general anesthesia, see below)—and when required, muscle relaxation treatments are provided.

Non-invasive monitors that help anesthesia providers gauge the adequacy of hypnosis and muscle relaxation do exist.

However, the adequacy level of anti-nociception provided preemptively or in response to a nociceptive stimulus in an anesthetized patient is typically assessed using surrogate measures, such as heart rate, blood pressure, tearing, pupillary response, and sweating. Yet, these surrogate measures are influenced by other factors, not related to nociception, such as hypoxia, hypercarbia, hypo- or hyperthermia, and medications and their reliability therefore uncertain. This uncertainty and the lack of objective evaluation of nociception, result in a large variability in dosing of opioids, the primary drugs used to treat moderate to surgical nociception.

Excessive or insufficient doses of opioids carry negative consequences to the patient in terms of both symptoms and outcomes. Awareness under anesthesia and inadvertent patient movement, which are totally preventable using the currently available monitors for hypnosis and muscle relaxation, were more common prior to the introduction of these monitors into common anesthesia practice. Excessive or insufficient opioid dosing has likewise a range of negative consequences, that can be prevented using adequate nociceptive monitoring.

Intraoperative opioids overdose has recognized clinical consequences including (i) delayed recovery of spontaneous ventilation upon emergence from general anesthesia; (ii) delayed return of consciousness upon emergence from general anesthesia (iii) increased risk of arterial hypotension in the absence (or upon low intensity) nociceptive stimulation related to a lower sympathetic tone; (v) risk of post-operative opioid-induced hyperalgesia resulting in increased pain levels and increased analgesic requirements, both in the acute and long term post-operative periods (Santonocito C. 2018).

Intraoperative opioids underdosing has been associated with undesirable intra-operative effects (movement, hemodynamic instability) and long-term effects of excessive activation of the sympathetic nervous system (Chen A. 2015).

Balanced anesthesia combines drugs to minimize the side effects of individual anesthetic drugs: operationally, (a) hypnosis is evoked by hypnotics/general anesthetics (e.g. midazolam, propofol, halogenated agents, ketamine etc.); (b) anti-nociception is induced by analgesics (opioids, non-opioids, regional analgesics, opioid-free technique), and (c) muscle relaxation is induced by neuromuscular blockers.

SUMMARY

Aspects of the disclosure, in some embodiments thereof, relate to perioperative pain management, in particular to perioperative pain management during general anesthesia.

Specifically, the present disclosure relates to device, system and method for perioperative pain management based on monitoring of a plurality (at least 2) of physiological parameters which when computationally combined, using machine learning techniques, provide a nociception index value. Advantageously, the herein disclosed device and method further provides the ability to interpret the nociception index value, in view of various clinical concerns and/or physical signs, to provide a treatment recommendation to caregivers, in particular anesthesiologists and critical care clinicians, ensuring optimal perioperative pain management. Additionally, or alternatively, the nociception index value, when interpreted in view of certain clinical concerns and/or physical signs, can then be applied to automatically provide an analgesic to the patient. That is, the processing unit configured to compute the nociception index value and to interpret the value in view of clinical concerns and/or physical signs may provide instructions to an infusion pump in a closed-loop configuration, such that the analgesic be provided at a desired time and dose to the patient without necessitating intervention/instructions by an anesthesiologists or other caregiver.

According to some embodiments, there is provided a device comprising a processing unit or a non-transitory computer readable medium having stored thereon software instructions that, when executed by a processor, cause the processor to receive a plurality of nociception-related physiological parameters of a patient from at least one physiological sensor, receive or derive an indication regarding a physiological signal related clinical concern, compute a nociception index value indicative of a level of nociception of the patient by applying a machine learning algorithm on the plurality of nociception-related physiological parameters and/or features derived therefrom, compare the nociception index value to a first threshold value indicative of an upper limit of nociceptive-anti-nociceptive balance (NANB) and to a second threshold value indicative of a lower limit of NANB; and provide a control output based on the comparison and on the indication relating to the physiological signal related clinical concern, wherein the control output comprises a displayed recommendation regarding operation of a medicament administration device or an operational command affecting operation of the medicament administration device.

According to some embodiments, the indication relating to the physiological signal related clinical concern is a blood pressure related clinical concern, a heart rate related clinical concern, an EEG related clinical concern or any combination thereof.

According to some embodiments, the indication relating to the physiological signal related clinical concern comprises one or more of hypertension, hypotension, tachycardia, hemodynamic instability, arrhythmia.

According to some embodiments, the indication relating to the physiological signal related clinical concern is a mean arterial blood pressure at or above a predetermined upper threshold value (MAP_HT mmHg) or a heart rate above a predetermined upper threshold value (HR-HT BPM).

According to some embodiments, when the mean arterial blood pressure is at or above a predetermined upper threshold value (MAP_HT mmHg) or and/the heart rate above a predetermined upper threshold value (HR-HT BPM and the nociception index value exceeds the first threshold value during a predetermined amount of monitoring time, providing the control output comprises providing to the medicament administration device a recommendation or a command to increase the dose of analgesic. According to some embodiments, the providing of the control output further comprises providing to the medicament administration device a recommendation or a command to administer a hypotensive agent if the mean arterial blood pressure remains about MAP_HT mmHg or above for a predetermined amount of time after the providing of the increased dose of the analgesic.

According to some embodiments, when the mean arterial blood pressure is at or above a predetermined upper threshold value (MAP_HT mmHg) or and/the heart rate above a predetermined upper threshold value (HR-HT BPM and the nociception index value is between the first threshold value and the second threshold value during a predetermined amount of monitoring time, providing the control output comprises providing to the medicament administration device a recommendation or a command to administer a hypotensive agent. According to some embodiments, the treatment further comprises increasing the dose of analgesic when the mean arterial blood pressure remains about MAP_HT mmHg for a predetermined amount of time after the providing the hypotensive agent.

According to some embodiments, when the mean arterial blood pressure is at or above a predetermined upper threshold value (MAP_HT mmHg) or and/the heart rate above a predetermined upper threshold value (HR-HT BPM and the nociception index value is beneath the second threshold value during a predetermined amount of monitoring time, providing the control output comprises providing to the medicament administration device a recommendation or a command to reduce the dose of analgesic and to administer a hypotensive agent.

According to some embodiments, the indication relating to the physiological signal related clinical concern is a mean arterial blood pressure at or below a predetermined lower threshold value (MAP_LT mmHg), a %-decrease in mean arterial blood pressure relative to a baseline mean arterial blood pressure (MAP_REL) of about 15% or above, or a heart rate at or below a predetermined lower threshold value (HR_LT BPM).

According to some embodiments, when the mean arterial blood pressure is at or below a predetermined lower threshold value (MAP_LT mmHg), the %-decrease in mean arterial blood pressure relative to a baseline mean arterial blood pressure (MAP_REL) of about 15% or above, and/or the heart rate is at or below a predetermined lower threshold value (HR_LT BPM), the method further includes obtaining and/or requesting an input regarding an absolute and/or relative hypovolemia value.

According to some embodiments, when the hypovolemia value is at or below a predetermined lower threshold value (Hypo_LT), providing the control output comprises providing to the medicament administration device a recommendation or a command to provide drip of fluids, to administer a vasoconstrictor, to decrease the dose of analgesic or any combination thereof.

According to some embodiments, when the nociception index value exceeds the first threshold value during a predetermined amount of monitoring time and an EEG of the patient is below a predetermined lower threshold value (EEG_LT), or a burst suppression ratio is above 0, providing the control output comprises providing to the medicament administration device a recommendation or a command to reduce concentration of hypnotic agent and increase the dose of analgesic.

According to some embodiments, when the nociception index value is between the first threshold value and the second threshold value during a predetermined amount of monitoring time, providing the control output comprises providing to the medicament administration device a recommendation or a command to provide a sympathomimetic/adrenergic agent.

According to some embodiments, when the nociception index value is beneath the second threshold value during a predetermined amount of monitoring time, providing the control output comprises providing to the medicament administration device a recommendation or a command to reduce the dose of analgesic.

According to some embodiments, when the nociception index value is about twice the first threshold value or more, providing the control output comprises providing to the medicament administration device a recommendation or a command to increase the dose of analgesic.

According to some embodiments, the method further includes receiving an indication regarding regional block effectiveness. According to some embodiments, when the nociception index value exceeds the first threshold value during a predetermined amount of monitoring time and effective regional block not confirmed, providing the control output comprises providing to the medicament administration device a recommendation or a command to increase dose of analgesic. According to some embodiments, when the nociception index value is below the second threshold value during a predetermined amount of monitoring time and effective regional block confirmed, providing the control output comprises providing to the medicament administration device a recommendation or a command to lower hypnotic agent to lowest possible concentration and/or to reduce the dose/concentration of opioid.

According to some embodiments, method further includes calibrating the NANB of the patient and/or an initial dose of analgesic provided to the patient, based on one or more patient specific parameters. According to some embodiments, the one or more patient specific parameters comprise age, BMI, gender, type of procedure, presence or not of local analgesia, co-morbidity chronic medication, genetic profile or any combination thereof.

According to some embodiments, the at least physiological sensor is selected from a PPG sensor, an accelerometer, a temperature sensor, blood pressure sensor, blood volume sensor, blood volume pulse, respiration sensor, near infrared spectroscopy sensor, a diffused correlation spectroscopy (DCS) sensor, an acoustics sensor, a bio-impedance sensor, a piezoelectric sensor, an EEG sensors, an EOG sensor, a video camera, a thermal camera, an RF sensor, an infrared sensor and any combination thereof.

According to some embodiments, the at least physiological sensor comprise a Photoplethysmograph (PPG) or a Galvanic Skin Response (GSR) sensor and wherein the plurality of nociception-related physiological parameters comprise at least two physiological parameters selected from: pulse rate, pulse rate variability, pulse wave amplitude, skin conductance level, and skin conductance fluctuations. According to some embodiments, the at least physiological sensors further comprise peripheral temperature (Temp) sensor and an accelerometer (ACC) and wherein the plurality of nociception-related physiological parameters comprises skin temperature, and movement.

According to some embodiments, the medicament administration device is selected from an infusion pump, an implantable pump or an inhalation device.

According to some embodiments, the patient is an anesthetized patient.

According to some embodiments, there is provided a system comprising a monitoring unit comprising at least one physiological sensor configured to monitor a plurality of nociception-related physiological parameters of the patient; and a processing unit configured to receive a plurality of nociception-related physiological parameters of a patient from at least two physiological sensors, receive or derived an indication regarding a physiological signal related clinical concern; compute a nociception index value indicative of a level of nociception of the patient by applying a machine learning algorithm on the plurality of nociception-related physiological parameters and/or features derived therefrom; compare the nociception index value to a first threshold value indicative of an upper limit of nociceptive-anti-nociceptive balance (NANB) and to a second threshold value indicative of a lower limit of NANB; and provide a control output based on the comparison and on the indication relating to the physiological signal related clinical concern, wherein the control output comprises a displayed recommendation regarding operation of a medicament administration device or an operational command affecting operation of the medicament administration device, as essentially described herein.

According to some embodiments, the system further comprises the medicament administration device. According to some embodiments, the medicament administration device is selected from an infusion pump, an implantable pump or an inhalation device.

According to some embodiments, there is provided a method (e.g. a compute implemented method or computer implemented instructions) for determining a nociceptive status of a patient. According to some embodiments, the method may in the form of non-transitory computer readable instructions that, when executed by a processor, cause the processor to receive a plurality of nociception-related physiological parameters of a patient from at least one physiological sensor, receive or derive an indication regarding a physiological signal related clinical concern, and compute (using the processing unit) a nociception index value indicative of a level of nociception of the patient by applying a machine learning algorithm on the plurality of nociception-related physiological parameters and/or features derived therefrom.

According to some embodiments, the method further includes comparing the nociception index value to a first threshold value indicative of an upper limit of nociceptive-anti-nociceptive balance (NANB) and to a second threshold value indicative of a lower limit of NANB; and providing a control output based on the comparison and on the indication relating to the physiological signal related clinical concern. According to some embodiments, the control output may be a displayed recommendation regarding operation of a medicament administration device or an operational command affecting operation of the medicament administration device.

According to some embodiments, the indication relating to the physiological signal related clinical concern is a blood pressure related clinical concern, a heart rate related clinical concern, an EEG related clinical concern or any combination thereof. According to some embodiments, the indication relating to the physiological signal related clinical concern comprises one or more of hypertension, hypotension, tachycardia, hemodynamic instability, arrhythmia.

According to some embodiments, the indication relating to the physiological signal related clinical concern is a mean arterial blood pressure at or above a predetermined upper threshold value (MAP_HT mmHg) or a heart rate above a predetermined upper threshold value (HR-HT BPM).

According to some embodiments, when the mean arterial blood pressure is at or above a predetermined upper threshold value (MAP_HT mmHg) or and/the heart rate above a predetermined upper threshold value (HR-HT BPM and the nociception index value exceeds the first threshold value during a predetermined amount of monitoring time, providing the control output comprises providing to the medicament administration device a recommendation or a command to increase the dose of analgesic. According to some embodiments, the providing of the control output further comprises providing to the medicament administration device a recommendation or a command to administer a hypotensive agent if the mean arterial blood pressure remains about MAP_HT mmHg or above for a predetermined amount of time after the providing of the increased dose of the analgesic.

According to some embodiments, when the mean arterial blood pressure at or above a predetermined upper threshold value (MAP_HT mmHg) or and/the heart rate above a predetermined upper threshold value (HR-HT BPM and the nociception index value is between the first threshold value and the second threshold value during a predetermined amount of monitoring time, providing the control output comprises providing to the medicament administration device a recommendation or a command to administer a hypotensive agent. According to some embodiments, the treatment further comprises increasing the dose of analgesic when the mean arterial blood pressure remains about MAP_HT mmHg for a predetermined amount of time after the providing the hypotensive agent.

According to some embodiments, when the mean arterial blood pressure at or above a predetermined upper threshold value (MAP_HT mmHg) or and/the heart rate above a predetermined upper threshold value (HR-HT BPM and the nociception index value is beneath the second threshold value during a predetermined amount of monitoring time, providing the control output comprises providing to the medicament administration device a recommendation or a command to reduce the dose of analgesic and to administer a hypotensive agent.

According to some embodiments, the indication relating to the physiological signal related clinical concern is a mean arterial blood pressure at or below a predetermined lower threshold value (MAP_LT mmHg), a %-decrease in mean arterial blood pressure relative to a baseline mean arterial blood pressure (MAP_REL) of about 15% or above, or a heart rate at or below a predetermined lower threshold value (HR_LT BPM).

According to some embodiments, when the mean arterial blood pressure at or below a predetermined lower threshold value (MAP_LT mmHg), the %-decrease in mean arterial blood pressure relative to a baseline mean arterial blood pressure (MAP_REL) of about 15% or above, and/or the heart rate is at or below a predetermined lower threshold value (HR_LT BPM), the device is further configured to obtain and/or request input regarding an absolute and/or relative hypovolemia value.

According to some embodiments, when the hypovolemia value is at or below a predetermined lower threshold value (Hypo_LT), providing the control output comprises providing to the medicament administration device a recommendation or a command to provide drip of fluids, to administer a vasoconstrictor, to decrease the dose of analgesic or any combination thereof.

According to some embodiments, when the nociception index value exceeds the first threshold value during a predetermined amount of monitoring time and an EEG of the patient is below a predetermined lower threshold value (EEG LT), or a burst suppression ratio is above 0, providing the control output comprises providing to the medicament administration device a recommendation or a command to reduce concentration of hypnotic agent and increase the dose of analgesic.

According to some embodiments, when the nociception index value is between the first threshold value and the second threshold value during a predetermined amount of monitoring time, providing the control output comprises providing to the medicament administration device a recommendation or a command to provide a sympathomimetic/adrenergic agent.

According to some embodiments, when the nociception index value is beneath the second threshold value during a predetermined amount of monitoring time, providing the control output comprises providing to the medicament administration device a recommendation or a command to reduce the dose of analgesic.

According to some embodiments, when the nociception index value is about twice the first threshold value or more, providing the control output comprises providing to the medicament administration device a recommendation or a command to increase the dose of analgesic.

According to some embodiments, the device is further configured to receive an indication regarding regional block effectiveness. According to some embodiments, when the nociception index value exceeds the first threshold value during a predetermined amount of monitoring time and effective regional block not confirmed, providing the control output comprises providing to the medicament administration device a recommendation or a command to increase dose of analgesic. According to some embodiments, when the nociception index value is below the second threshold value during a predetermined amount of monitoring time and effective regional block confirmed, providing the control output comprises providing to the medicament administration device a recommendation or a command to lower hypnotic agent to lowest possible concentration and/or to reduce the dose/concentration of opioid.

According to some embodiments, the processing circuit is further configured to calibrate the NANB of the patient and/or an initial dose of analgesic provided to the patient, based on one or more patient specific parameters.

According to some embodiments, the one or more patient specific parameters comprise age, BMI, gender, type of procedure, presence or not of local analgesia, co-morbidity chronic medication, genetic profile or any combination thereof.

According to some embodiments, the at least physiological sensor comprise a Photoplethysmograph (PPG) or a Galvanic Skin Response (GSR) sensor and wherein the plurality of nociception-related physiological parameters comprise at least two physiological parameters selected from: pulse rate, pulse rate variability, pulse wave amplitude, skin conductance level, and skin conductance fluctuations. According to some embodiments, the at least physiological sensors further comprise peripheral temperature (Temp) sensor and an accelerometer (ACC) and wherein the plurality of nociception-related physiological parameters comprises skin temperature, and movement.

According to some embodiments, the at least physiological sensor is selected from a PPG sensor, an accelerometer, a temperature sensor, blood pressure sensor, blood volume sensor, blood volume pulse, respiration sensor, near infrared spectroscopy sensor, a diffused correlation spectroscopy (DC S) sensor, an acoustics sensor, a bio-impedance sensor, a piezoelectric sensor, an EEG sensors, an EOG sensor, a video camera, a thermal camera, an RF sensor, an infrared sensor and any combination thereof.

According to some embodiments, the device further comprises the medicament administration device. According to some embodiments, the medicament administration device is selected from an infusion pump, an implantable pump or an inhalation device.

According to some embodiments, the patient is an anesthetized patient.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided device, system and method for perioperative pain management.

Pain is a descriptor of a conscious, emotional, subjective experience generated by a wide variety of events. Tissue damage-associated acute pain consists of both physiological and psychological characters. During general anesthesia, the conscious experience of pain is cancelled. Hence, in an anesthetized patient it is not appropriate to call 'pain' the physiological reaction to tissue aggression by surgery.

Instead, surgical stimulus, with its immediate consequences on system function and without the higher order processing that is defined as consciousness, is designated as 'nociception'. This term covers the integrated organism response caused by tissue damage, from the peripheral sensory afferent pathway to the brainstem and cortical levels, where nociception may manifest as cardiovascular, hormonal and neurological responses.

Us used herein the term "perioperative" with regards to nociception management refers to nociception management prior to (preemptive), at the beginning (induction), during (maintenance), and post—a surgical procedure that attenuate or eliminate the nociceptive response to expected surgical nociceptive stimuli. According to some embodiments, the method may be method for managing nociception during the maintenance period of a surgical procedure.

According to some embodiments, there is provided a device for providing optimal nociception management to a patient, including but not exclusively an anesthetized patient. The device including a processing unit configured to receive a plurality of nociception-related physiological parameters of a patient from at least one physiological sensor or to derive a plurality of nociception-related physiological parameters of a patient from one or more physiological signals obtained from at least one physiological sensors; receive or derive an indication regarding a physiological signal related clinical concern; compute a nociception index value indicative of a level of nociception of the patient by applying a machine learning algorithm on the plurality of nociception-related physiological parameters and/or features derived therefrom; compare the nociception index value to a first threshold value indicative of an upper limit of nociceptive-anti-nociceptive balance (NANB) and to a second threshold value indicative of a lower limit of NANB; and provide a control output based on the comparison and on the indication relating to the physiological signal related clinical concern, wherein the control output comprises a displayed recommendation regarding operation of a medicament administration device or an operational command affecting operation of the medicament administration device.

As used herein, the term "plurality of nociception-related physiological parameters" may refer to 2 or more, 3 or more, 4 or more, 5 or more, 10 or more or 15 or more nociception-related physiological parameters. Each possibility is a separate embodiment. According to some embodiments, the plurality of nociception-related physiological parameters may be selected from pulse rate, pulse rate variability, pulse wave amplitude, skin conductance level, and skin conductance fluctuations, skin temperature, and movement and any combination thereof. Each possibility is a separate embodiment.

According to some embodiments, all of the nociception-related physiological parameters may be derived from a same physiological signal. According to some embodiments, all of the nociception-related physiological parameters may be derived from at least two different physiological signals, e.g. 2, 3, 4, 5 or more physiological signals. Each possibility is a separate embodiment. According to some embodiments, the at least two different physiological signals may be obtained from a same physiological sensor. According to some embodiments, the at least two different physiological signals may be obtained from at least two different physiological sensors e.g. 2, 3, 4, 5 or more physiological signals. Each possibility is a separate embodiment.

According to some embodiments, the at least one physiological sensor may include at least a Photoplethysmograph (PPG) and/or a Galvanic Skin Response (GSR) sensor. According to some embodiments, the at least one sensor may further include a temperature sensor and/or an accelerometer.

According to some embodiments, the at least one physiological sensor may include at least at least one sensor selected from a PPG sensor, an accelerometer, a temperature sensor, blood pressure sensor, blood volume sensor, blood volume pulse, respiration sensor, near infrared spectroscopy sensor, a diffused correlation spectroscopy (DCS) sensor, an acoustics sensor, a bio-impedance sensor, a piezoelectric sensor, EEG sensors, EOG sensors and any combination thereof. Each possibility is a separate embodiment.

According to some embodiments, the at least one physiological sensor may be or include non-touch sensor such as, but not limited to, a video camera, a thermal camera, an RF sensor, an infrared sensor, or any other sensor capable of sensing/monitoring physiological signal from a distance. Each possibility is a separate embodiment.

According to some embodiments, computing the nociception index value comprises deriving/extracting the plurality of physiological parameters and/or features from the physiological signal and applying a non-linear classification algorithm thereon.

According to some embodiments, the NANB may be patient specific. According to some embodiments, the processing circuit may be configured to set and/or calibrate the NANB of the patient and/or an initial dose of analgesic provided to the patient, based on one or more patient specific parameters. Non-limiting examples of patient specific parameters age, BMI, gender, type of procedure, presence or not of local analgesia, co-morbidity chronic medication, genetic profile or any combination thereof. Each possibility is a separate embodiment.

As used herein, receiving an indication regarding a physiological signal related clinical concern may refer to obtain a physiological signal or a processed parameter derived from a physiological signal from an external monitor, such as but not limited to an external heart rate monitor and the like. Additionally or alternatively, receiving an indication regarding a physiological signal related clinical concern may refer to obtaining or deriving a physiological signal from one or more of the same at least one physiological sensor from which the plurality of nociception-related physiological parameters are derived. Additionally or alternatively, receiving an indication regarding a physiological signal related clinical concern may refer to receiving an input, e.g. through a user interface, regarding a physiological concern. For example, a medical doctor may input the indication due to an output received from another monitor.

According to some embodiments, the clinical concern may be a blood pressure related clinical concern, a heart rate related clinical concern, an EEG related clinical concern or any combination thereof. Each possibility is a separate embodiment. According to some embodiments, the clinical concern may be hypertension, hypotension, tachycardia, hemodynamic instability, arrhythmia or any suitable combination thereof. Each possibility is a separate embodiment.

According to some embodiments, the clinical concern may be a mean arterial blood pressure at or above a predetermined upper threshold value (MAP_HT mmHg) or a heart rate above a predetermined upper threshold value (HR-HT BPM).

According to some embodiments, when the mean arterial blood pressure is at or above a predetermined upper threshold value (MAP_HT mmHg) and/or the heart rate above a predetermined upper threshold value (HR-HT BPM) and the computed nociception index value exceeds a first upper threshold value for a predetermined amount of monitoring time, the control circuit may be configured to provide a recommendation to increase the dose of analgesic provided to the patient (open loop) or to provide a command to a medicament administration device to automatically increase the dose of analgesic (closed loop). According to some embodiments, the control circuit may be configured to provide a recommendation to administer a hypotensive agent if the mean arterial blood pressure remains about MAP_HT mmHg or above for a predetermined amount of time after the providing of the increased dose of the analgesic or to provide a command to a medicament administration device to administer a hypotensive agent if the mean arterial blood pressure remains about MAP_HT mmHg or above for a predetermined amount of time after the providing of the increased dose of the analgesic.

According to some embodiments, the recommendation may be an output message displayed. Additionally or alternatively, the recommendation may be a request to "OK" to increase the dose of an analgesic. Additionally or alternatively, the recommendation may turn into an automatic command unless counteracted by a "reject" within a certain amount of time (e.g. unless rejected (e.g. by an anesthesiologist) within 5 seconds from it being displayed).

It is understood by one of ordinary skill in the art that in general, a recommendation/command to increase the dose of analgesic or other medicament may only be provided as long as the dose currently provided to the patient is below a maximal recommended dose. It is further understood that the maximal recommended dose depends on the patient, his medical status, the type of analgesic (or other medicament) administered etc. According to some embodiments, the degree of the increase may be patient specific. According to some embodiments, the degree of the increase may be based on the degree by which the threshold is exceeded and/or on the one or more patient specific parameters e.g. age, BMI, gender, type of procedure, presence or not of local analgesia, co-morbidity chronic medication, genetic profile or any combination thereof.

Non-limiting examples of suitable analgesics include opioid-like analgesics, such as, but not limited to, Fentanyl, Sufentanyl, Remifentanyl and Alfentanil and opioid-free analgesic, such as, but not limited to, Dexmedetomidine, Lidocaine, Ketamine, Gabapentinoids, Magnesium Sulfate, Alpha-2 adrenoreceptor agonists and Beta-Blockers. Each possibility is a separate embodiment. It is understood that the maximal recommended dose as well as increments in dose increase/reduction may depend on the type of analgesics, e.g. whether opioid-like or opioid-free, whether taken alone or in a "cocktail" with other analgesics, the specific analgesic itself as well as on patient parameters (e.g. age weight, gender and medical history).

According to some embodiments, when the mean arterial blood pressure is at or above the predetermined upper threshold value (MAP_HT mmHg) and/or the heart rate is above the predetermined upper threshold value (HR-HT BPM) and the computed nociception index value is between the first upper threshold value and the second lower threshold value during a predetermined amount of monitoring time, the control circuit may be configured to provide a recommendation to administer a hypotensive agent (initiate or increase dose) or to provide a command to a medicament administration device to administer a hypotensive agent (initiate or increase dose). According to some embodiments, the control circuit may be configured to provide a recommendation to increase the dose of analgesic if the mean arterial blood pressure remains about MAP_HT mmHg for a predetermined amount of time after the providing the hypotensive agent or to provide a command to increase the dose of analgesic if the mean arterial blood pressure remains about MAP_HT mmHg for a predetermined amount of time after the providing the hypotensive agent.

According to some embodiments, when the mean arterial blood pressure is at or above a predetermined upper threshold value (MAP_HT mmHg) and/or the heart rate above the predetermined upper threshold value (HR-HT BPM) and the computed nociception index value is beneath the second (lower) threshold value during a predetermined amount of monitoring time, the control circuit may be configured to provide a recommendation to reduce the dose of analgesic and to administer a hypotensive agent or to provide a command to a medicament administration device to administer reduce the dose of analgesic.

It is understood by one of ordinary skill in the art that in general, a recommendation/command to increase the dose of analgesic may only be provided as long as the dose currently provided to the patient is above a minimal recommended dose. According to some embodiments, the degree of the decrease may be patient specific. According to some embodiments, the degree of the decrease may be based on the degree by which is beneath the second threshold value and/or on the one or more patient specific parameters e.g. age, BMI, gender, type of procedure, presence or not of local analgesia, co-morbidity chronic medication, genetic profile or any combination thereof.

According to some embodiments, the clinical concern may be a mean arterial blood pressure at or below a predetermined lower threshold value (MAP_LT mmHg), a %-decrease in mean arterial blood pressure relative to a baseline mean arterial blood pressure (MAP_REL) of about 15% or above, and/or a heart rate at or below a predetermined lower threshold value (HR_LT BPM).

According to some embodiments, when the mean arterial blood pressure is at or below a predetermined lower threshold value (MAP_LT mmHg), the %-decrease in mean arterial blood pressure relative to a baseline mean arterial blood pressure (MAP_REL) of about 15% or above, and the heart rate at or below a predetermined lower threshold value (HR_LT BPM), the processing circuit may be further request input regarding an absolute and/or relative hypovolemia value. and wherein if the nociception index value exceeds the first threshold value during a predetermined amount of monitoring time.

According to some embodiments, when the mean arterial blood pressure is at or below a predetermined lower threshold value (MAP_LT mmHg), the %-decrease in mean arterial blood pressure relative to baseline mean arterial blood pressure (MAP_REL) of about 15% or above, the heart rate at or below a predetermined lower threshold value (HR_LT BPM), and the hypovolemia value is at or below a predetermined lower threshold value (Hypo_LT), the control circuit may be configured to provide a recommendation or a command to provide drip of fluids, to administer a vasoconstrictor, to decrease the dose of analgesic or any combination thereof.

According to some embodiments, when the mean arterial blood pressure is at or below a predetermined lower threshold value (MAP_LT mmHg), the %-decrease in mean arterial blood pressure relative to baseline mean arterial blood pressure (MAP_REL) of about 15% or above, the heart rate at or below a predetermined lower threshold value (HR_LT BPM), and the hypovolemia value is at or below a predetermined lower threshold value (Hypo_LT), and the nociception index value exceeds the first (upper) threshold value during a predetermined amount of monitoring time, an EEG of the patient is below a predetermined lower threshold value (EEG LT), or a burst suppression ratio is above 0, the control circuit may be configured to provide a recommendation or a command to reduce concentration of hypnotic agent and increase the dose of analgesic.

According to some embodiments, when the mean arterial blood pressure is at or below a predetermined lower threshold value (MAP_LT mmHg), the %-decrease in mean arterial blood pressure relative to baseline mean arterial blood pressure (MAP_REL) of about 15% or above, the heart rate at or below a predetermined lower threshold value (HR_LT BPM), and the hypovolemia value is at or below a predetermined lower threshold value (Hypo_LT), and the nociception index value is between the first threshold value and the second threshold value during a predetermined amount of monitoring time, the control circuit may be configured to provide a recommendation or a command to provide a sympathomimetic/adrenergic agent.

According to some embodiments, when the mean arterial blood pressure is at or below a predetermined lower threshold value (MAP_LT mmHg), the %-decrease in mean arterial blood pressure relative to baseline mean arterial blood pressure (MAP_REL) of about 15% or above, the heart rate at or below a predetermined lower threshold value (HR_LT BPM), and the hypovolemia value is at or below a predetermined lower threshold value (Hypo_LT), and the nociception index value is at or beneath the second threshold value during a predetermined amount of monitoring time, the control circuit may be configured to provide a recommendation or a command to reduce the dose of analgesic.

According to some embodiments, irrespective of the nature of the clinical concern, in case of a nociception index value is about twice the first threshold value or more, the control circuit may be configured to provide a recommendation or a command to increase the dose of analgesic.

According to some embodiments, the processing circuit may be further configured to receive an indication regarding regional block effectiveness. According to some embodiments, regional block effectiveness may be verified by computing a nociception index value after and optionally also before providing a nociceptive stimulus to the region targeted by the block.

According to some embodiments, if effective regional block is confirmed yet the nociception index value exceeds the first threshold value during a predetermined amount of monitoring time, the control circuit may be configured to provide a recommendation or a command to increase dose of analgesic.

According to some embodiments, if effective regional block is confirmed and the nociception index value is below the second threshold value during a predetermined amount of monitoring time, the control circuit may be configured to provide a recommendation or a command to lower the dose of hypnotic agent to a lowest possible concentration and/or to reduce the dose/concentration of opioid.

According to some embodiments, there is provided a system comprising a monitoring unit comprising at least one (such as 1, 2, 3, 4, 5 or more), preferably non-invasive, physiological sensor configured to monitor a plurality of nociception-related physiological parameters of the patient; and the herein disclosed processing unit.

According to some embodiments, the monitoring unit may include a Photoplethysmograph (PPG), a Galvanic Skin Response (GSR) sensor, a temperature sensor, an accelerometer or any combination thereof. Each possibility is a separate embodiment.

According to some embodiments, the at least one physiological sensor may include at least at least one sensor selected from a PPG sensor, an accelerometer, a temperature sensor, blood pressure sensor, blood volume sensor, blood volume pulse, respiration sensor, near infrared spectroscopy sensor, a diffused correlation spectroscopy (DCS) sensor, an acoustics sensor, a bio-impedance sensor, a piezoelectric sensor, EEG sensors, EOG sensors and any combination thereof. Each possibility is a separate embodiment.

According to some embodiments, the system further includes the medicament administration device. According to some embodiments, the medicament administration device is selected from an infusion pump, an implantable pump, an inhalation device or any combination thereof. Each possibility is a separate embodiment.

Figure 4:
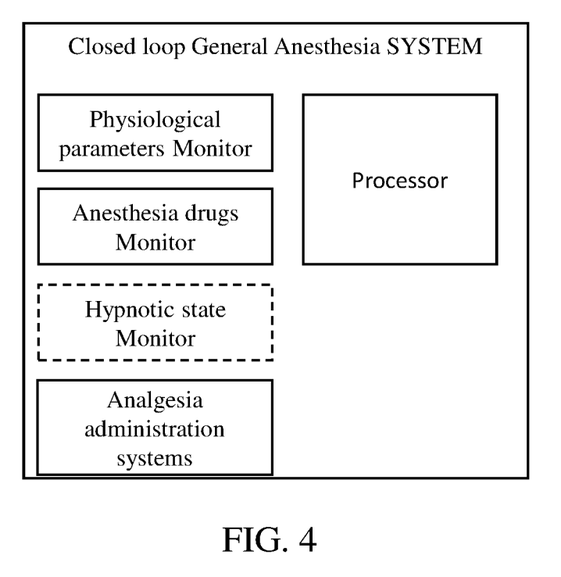
FIG. 4 illustratively depict a perioperative nociception management module, according to some embodiments.
Figure 5:
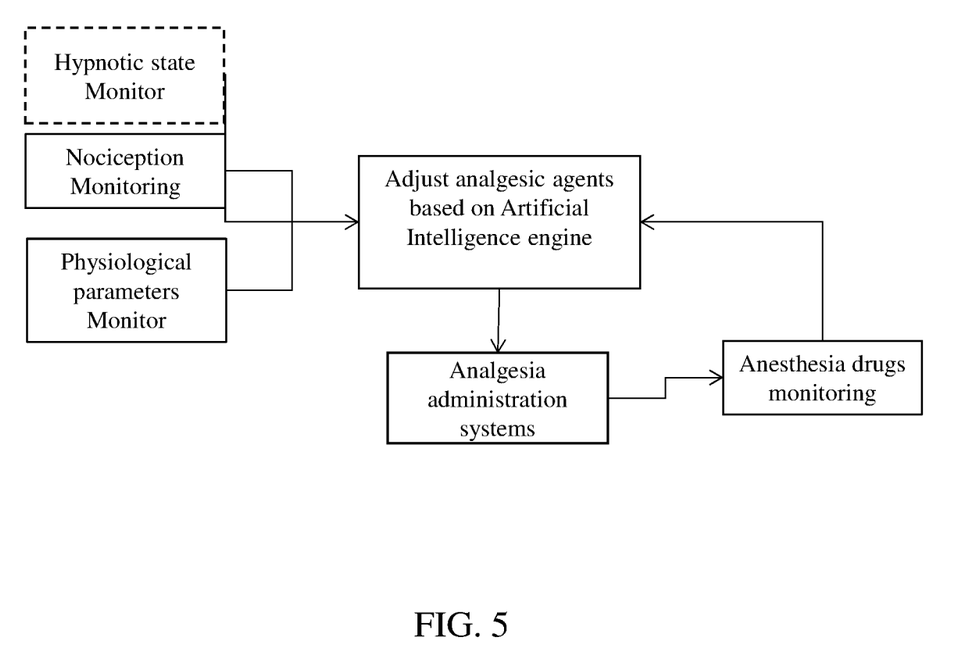
FIG. 5 illustratively depict a processing unit for perioperative nociception management, according to some embodiments.

According to some embodiments, the device and method include monitoring a plurality of nociception-related physiological parameters of the patient using at one physiological sensors (see FIG. 4) and combining the plurality of nociception-related physiological parameters into a nociception index value (also referred to herein as NOL) indicative of a level of nociception of the patient, by applying a machine learning algorithm on the plurality of nociception-related physiological parameters and/or features derived therefrom (as essentially shown in FIG. 5).

By way of example, the nociception index value may vary between 0 and 100. Initially, the value may be derived from a preloaded population algorithm database using signals obtained in the absence of a noxious stimuli. As the patient's own data accumulates during the monitoring session, the calculation of the index value may be mainly based on the patient's own data with constant referral to previous time-derivatives of acquired parameters, optionally with a small fixed percent of population data integrated in the algorithm. According to some embodiments, the nociception index values that are acquired continuously during the procedure may be "smoothened" by the algorithm to prevent excessive fluctuations.

As the NOL index is very sensitive and values may fluctuate and change by seconds, the absolute NOL value together with the time above a certain value may be evaluated in order to clinically decide on the timing and dose needed. Fluctuations of the NOL value above the threshold for a few seconds should not generally be considered as suggesting a requirement for the administration of analgesics.

It is understood that a single fluctuation in the physiological parameters and/or in the NOL is not necessarily clinically significant. Accordingly, trends of at least 1 minute, at least 2 minutes or at least 5 minutes may be required to ensure clinically relevant information and reflect the nociceptive state of the patient. Similarly, a minimum of 1 minute, 2 minutes or five minutes of a NOL value above the first threshold may be recommendable before making a clinical intervention.

According to some embodiments, in order to determine the adequacy of nociception the computed nociception index value may then be compared to a first threshold value indicative of an upper limit of nociceptive-anti-nociceptive balance (NANB) and to a second threshold value indicative of a lower limit of NANB. As used herein, the term "nociceptive-anti-nociceptive balance (NANB)" refers to a value range of the nociception index value, which is indicative of an adequate nociception management.

Figure 1:
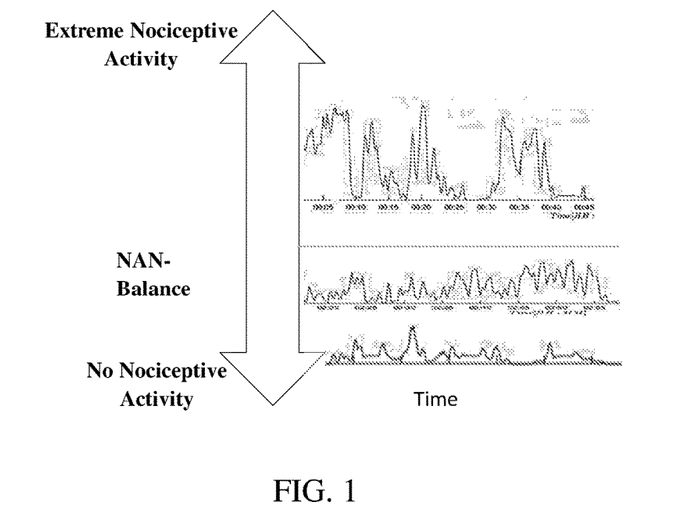
FIG. 1 shows an illustrative nociception index value scale with accompanying graphical results.

By way of example, during surgical stimulation under general anesthesia, a nociception index value of zero indicates no nociceptive response, and a nociception index value of 100 indicates extreme nociceptive response (see FIG. 1). Similarly, values between 10-25 may, as exemplified herein, represent NANB values, indicative of no nociception in the absence of noxious stimuli, or effective analgesia in the presence of noxious stimuli. Accordingly, according to some embodiments, the first threshold value may be a nociception index value of 25, which is identified as a cutoff value discriminating between noxious and non-noxious events and.

The hypnotic component of anesthesia has been traditionally separated from the NANB. However, according to some embodiments, a synergistic effect between hypnotic and analgesic drugs may exist. Accordingly, low concentrations of opioids may greatly (by more than 50%) increase the requirements for hypnotics. Similarly, there is a plateau level of opioid beyond which more opioids will not further decrease hypnotic requirements.

Accordingly, there is a need for carefully balancing the optimum combination of opioids and hypnotics, defined by the smallest doses (concentrations) of hypnotics/opioids that result in 'non-responsiveness' and provide a 50% reduction in hypnotics requirement.

Since clinicians are aware of the fluctuations in opioid's concentrations when administered by boluses (and therefore the movement along the hypnotics-opioids interactions graph); and because hypnotics concentrations are usually maintained at fairly constant levels either with inhalation or intravenous administration, there is a tendency to overdose the opioids at the beginning of surgery in order to achieve a "safer" concentration for a longer period of time and thus avoid "responsiveness". Given the fact that high concentrations of opioids prevent spontaneous ventilation and return of consciousness, there is a tendency to under dose patients in preparation of emergence from anesthesia during the last stages of surgery.

Advantageously, the herein disclosed device, system, method and accompanying algorithm is configured to determine the optimum combination of opioids and hypnotics based on an integrated analysis of the NOL value and specific clinical concerns and/or physical signs of the specific patient, i.e. in a patient tailored manner.

Figure 2:
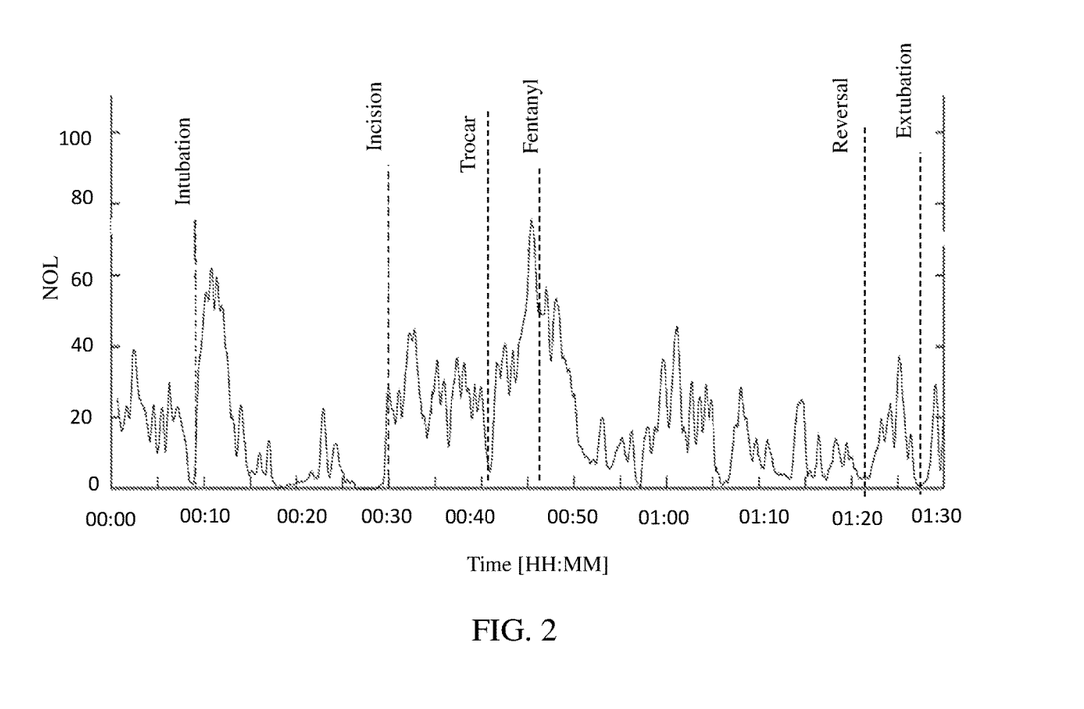
FIG. 2 is a graph showing nociception index (NOL) values over time during a surgery, with indication of events taking place during the surgery.

As a further advantage, the herein disclosed device, system, method and accompanying algorithm provides potentially useful information throughout the surgical session, which is typically divided into three phases, namely the induction phase (including the intubation phase if applicable), the maintenance phase (from start of surgery to end of sutures) and emergence phase (awakening and extubation if applicable), as exemplified in FIG. 2.

The Induction Phase:

According to some embodiments, prior to induction, the monitoring unit, including the herein disclosed one or more physiological sensors, is placed on or near the patient. According to some embodiments, the monitoring unit may be or include a finger probe configured for being positioned on the patient's finger. Additionally or alternatively, the monitoring unit may be or include a unit configured to be worn by the patient (e.g. around the wrist, around the chest or the like). Additionally or alternatively, the monitoring unit may be or include a non-touch sensor, such as a video camera, a thermal camera, an RF sensor, an infrared sensor, or any other sensor capable of sensing/monitoring physiological signal from a distance.

According to some embodiments, the induction period includes a short calibration period (e.g. about 30 seconds) during which no index value is displayed.

According to some embodiments, the first index value displayed is of the patient when still awake and reflects his/her basic sympathetic tone. The first value is typically higher than an index value obtained when the patient is anesthetized. By way of example, the first index value may range between 10-40, depending on the patient's stress level.

According to some embodiments, administration of induction drugs by the machine, may be based on a NOL baseline value or baseline value range (also referred to as ANG_Start) defined according to the patient age, BMI, gender, type of procedure, presence or not of local analgesia, co-morbidity chronic medication, genetic profile, or any other information relevant to the patient or combinations thereof. Each possibility is a separate embodiment. According to some embodiments, the NOL baseline value for the analgesics, may be determined according to a predefined table derived from or learned, based on population data. According to some embodiments, the NOL baseline value may be adapted/adjusted/optimized, based on learning on NOL values obtained from a population of patients undergoing intubation or laryngoscope insertion so as to ensure that the NOL values obtained during these procedures remain above a predetermined upper threshold value and below a predetermined lower threshold value.

According to some embodiments a threshold value may be a NOL peak value, a NOL area under the curve value, a NOL variation value, a NOL time above threshold, or any other NOL derived value. Each possibility is a separate embodiment. According to some embodiments, the ANG_Start may be used as a "desired" NOL value/value range which should be reached (e.g. by optimizing the dose of analgesic) prior to commencing incision. According to some embodiments, the ANG_Start may be used as a "desired" NOL value/value range, which should be reached when a button or an indication for "preemptive analgesia" is pushed.

The same logic applies to hypnotic medication with HYP_Start, when looking at the same manner on EEG indices such as but not limited to BIS, Entropy, QCon, SEF—Spectral edge frequency etc. Each possibility is a separate embodiment.

After administration of induction drugs, according to predefined parameters, the nociception index value typically drops, reflecting the NANB in the absence of a noxious stimulation with reduction of sympathetic tone due to loss of consciousness and administration of an analgesic. By way of example, an index value below 25 is typically expected. Of note, pressure on the mandible during mask ventilation can result in nociception index value values above threshold (>25).

As set forth above, intubation is part of the induction phase. Direct laryngoscopy using curved Macintosh blade is a standard tracheal intubation technique often used during general anesthesia [Levitan R M et al. 2011]. Providing an appropriate view of the glottis requires applying some force during laryngoscopy and intubation. Throat soreness or hoarseness accompanying intubation is typically painful for patients and may trigger a bad memory or dissatisfaction with the anesthesia procedure.

Advantageously, the herein disclosed nociception index value may prompt the clinician to observe the patient's NAN balance state and adjust the intubation technique and analgesia accordingly. According to some embodiments, and as essentially described above, once an input indication is provided e.g. through a user-interface, that intubation is about to initiated, the processer may instruct an infusion pump to provide a dose of an analgesic or other medicament required to reach a ANG_Start NOL or other predetermined NOL value/value range.

As a further advantage, the nociception index value can support the clinician when using different techniques of intubation or placement of airway devices (e.g., laryngeal mask airways or LMA), as well as choosing the most suitable technique. Moreover, the herein disclosed nociception index value may be utilized to guide dosing of analgesics during prolonged intubation attempts. According to some embodiment, the processer may instruct an infusion pump to provide a dose of an analgesic or other medicament required to reach an ANG_Start NOL value or another predetermined baseline value/value range when intubation prolongs.

According to some embodiments, for example if a target-controlled infusion (TCI) of opioids is used or if for a given dose of opioid the TCI profile is estimated by the clinician, the nociception index value may advantageously help "calibrate" the patient's analgesic requirement based on the value obtained during intubation and use this information for subsequent nociceptive stimuli (e.g. skin incision, other types of surgical nociceptive stimuli). According to some embodiment, the processer may instruct an infusion pump to provide a dose of an analgesic or other medicament required to reach a desired NOL maintenance value or value range. According to some embodiments, the NOL maintenance value may be determined and/or calibrated based on the NOL values or NOL value derivatives (e.g. NOL peak value, NOL area under the curve, a NOL variation value, or a NOL time above threshold) obtained during intubation. That is, according to some embodiments, the device analyzes parameters, such as the peak NOL values, and the area under curve of the peak, obtained during intubation, and based thereon, e.g. based on additional statistics of the NOL and the parameters, combines the NOL to set parameters used for providing analgesic during maintenance. For example, the dose increase may be multiplied by a certain factor (instead of increasing the dose in each step by Ang_Step, the increase will be by 1.5×Ang_Step).

Additionally or alternatively, the NOL maintenance value may be determined and/or calibrated based on a controlled nociceptive stimulus. As a non-limiting example, the controlled nociceptive stimulus may be an electrical stimulus and/or heat stimulus. A non-limiting example of an electrical stimulus may be 100 mA for 30 seconds. The input of the value of the stimulus (current or heat temperature), can be sent to the algorithm and the NOL values (or AUC or time above thresholds, or any similar matric), can be compared to a predefined data base (or evolving data base) and influence either the Ang_Step or the ANG_Start values in a similar manner as described above.

The Maintenance Phase:

As further elaborated herein, the herein disclosed nociception index value (NOL) can be utilized to obtain optimal nociception management during the surgery itself, i.e. from start of surgery (incision) to end of sutures.

For example, a recent clinical trial has demonstrated that adjustment of remifentanil dosing to maintain the nociception index value within a target range of 10 to 25 resulted in improved patient outcome as compared to standard clinical care and reduced the overall amount of remifentanil required to administer an optimal general anesthetic to adult patients (Meijer F S. 2019).

Moreover, it was demonstrated that by using NOL-guided analgesia in remifentanil TCI, the clinician may improve hemodynamic stability, as evidenced by fewer episodes of low heart rate (HR<50 bpm) and or low blood pressure (MAP<60 mmHg) (Meijer F S. 2019), (Edry R. 2016), (Martini C H 2015); decreased intraoperative use of pharmacologic agents to treat low blood pressure and low heart rate (i.e. vasopressors and beta-agonists); and shortened period to awakening and or extubation after surgery (Meijer F S. 2019).

In response to noxious stimulation, the NOL responses may be observed either in parallel with or independently of hemodynamic responses. This may enable the clinician to distinguish between hemodynamic and nociceptive response for elevated MAP and HR values. In general, changes in NOL in response to noxious stimuli have been shown to be more sensitive than changes in MAP or HR (Edry R. 2016) (Martini C H 2015).

According to some embodiments, NOL responses to stimulation may be markedly attenuated in a dose-dependent fashion upon opioid administration, e.g., fentanyl or remifentanil. Similarly, changes in the NOL-index trend with no changes in hemodynamic parameters (HR and MAP) during maintenance, warrant additional analgesic assessment.

Table 1 below describes the algorithm of the close loop or open loop analgesia and anesthesia maintenance carried out a monitoring module such as described in FIG. 4 and FIG. 5:

TABLE 1

| Clinical Concern | NOL | EEG | MAP & HR | Interventions (closed loop)- or pop up suggestion for intervention (open loop) | Recommendations & comments |
| --- | --- | --- | --- | --- | --- |
| High MAP and/or High HR | >NOL_HT for more than NOL_min_time min. | EEG_LT- EEG_HT | MAP- SBP > MAP_HT mmHg and/or HR- > HR HT BPM | Increase analgesic dosing by Ang_Step and repeat after INT_NOL_REPEAT min. until NOL < NOL_HT. But not to | Do not exceed maximum analgesic dose - MAX_ALG_DOSE maximum dose is |

TABLE 1-continued

| Clinical Concern | NOL | EEG | MAP & HR | Interventions (closed loop)- or pop up suggestion for intervention (open loop) | Recommendations & comments |
|---|---|---|---|---|---|
| | | | | exceed MAX_ALG_DOSE If MAP still > MAP_HT after 2 increases, add IV bolus of hypertensive agent and repeat INT_MAP_REPEAT min. | customized in advanced in the program, MAX_ALG_DOSE |
| | Below NOL_HT | | | IV bolus of hypertensive agent and repeat INT_MAP_REPEAT. until MAP < MAP_HT. If MAP still > < AP_HT after 2 iterations, add analgesic at Ang_Step. | |
| | Below NOL_LT | | | Add IV bolus of Sympathomimetic/ adrenergic drug such as Ca channel blocker or beta-blocker Reduce analgesic dosing by Ang_Step and repeat after INT_NOL_REPEAT min. until NOL > NOL_LT but not below MIN_ALG_DOSE | Administer a minimum analgesic dose but not less than MIN_ALG_DOSE |
| Low MAP And/or Low HR | >NOL_HT for more than NOL_min_time. | EEG_LT-EEG_HT | MAP - >20 MAP_REL % decrease from baseline or MAP < MAP_LT mmHg And/or HR - < HR_LT BPM | Obtain absolute/relative hypovolemia values In case hypovolemia values < Hypo_LT Increase rate of fluids drip follow followed by vasoconstrictors Otherwise increase analgesic dosing administer Sympathomimetic/ adrenergic drugs | not exceed maximum analgesic dose MAX_ALG_DOSE |
| | Below NOL_HT | | | | |
| | Below 10 | | | reducing analgesic dosing by Ang_Step and repeat after INT_NOL_REPEAT min. until NOL > NOL_LT but not below MIN_ALG_DOSE If analgesia is at minimum administer Sympathomimetic/ adrenergic drugs | administer a minimum analgesic dose but not below MIN_ALG_DOSE |
| | >NOL_HT for more than NOL_min_time | <EEG_LT-, especially if burst suppression ratio > 0 | | Correct hypnotic excessive dose/concentration if NOL still > NOL_HT, Based on the identified parameter administer Sympathomimetic/ adrenergic drugs, if NOL still > NOL_HT, increase analgesic dosing and repeat INT_NOL_REPEAT min. until NOL < NOL_HT but not above MAX_ALG_DOSE | |

TABLE 1-continued

| Clinical Concern | NOL | EEG | MAP & HR | Interventions (closed loop)- or pop up suggestion for intervention (open loop) | Recommendations & comments |
|---|---|---|---|---|---|
| Sudden increase in NOL upon application of nociceptive stimulus, patient moves | Above NOL_XHT | EEG_LT-EEG_HT | MAP ->MAP_REL % increase from baseline HR - HR_REL % increase from baseline | increase analgesic dosing and repeat INT_NOL_REPEAT min. until NOL < NOL_HT but not above MAX_ALG_DOSE. Give alert to stop stimulus. | Remark: Time to peak effect of opioid may be delayed for 5-6 minutes (fentanyl and sufentanil) |
|  | Above 60 |  |  | increase analgesic dosing and repeat INT_NOL_REPEAT min. until NOL < NOL_HT but not above MAX_ALG_DOSE Increase hypnotic concentration Send alert to stop nociceptive stimulus. |  |
| Confirming regional block effectiveness | Below NOL_HT | EEG_LT-EEG_HT | MAP -the risk of arterial hypotension may increase | Start with Min hypnotic concertation. Start with MIN_ALG_DOSE_With Regional and follow the above suggestion. Better titration with short acting opioids that may stop or reduced to MIN_ALG_DOSE_With Regional once regional block is effective. | Logic: According to the type of local anesthetic being used, time to peak effect may be delayed (depends on the drug's PK). |
|  | Above NOL_HT |  | MAP - arterial pressure may be variable | increase analgesic dosing and repeat INT_NOL_REPEAT min. until NOL < NOL_HT but not above MAX_ALG_DOSE Send an alert to stop the nociception stimulus, and alert that local analgesics might not be effective Assess the level of anesthesia | Confirms effectiveness of the regional block. |
| Opioid free analgesia | Below NOL_HT | EEG_LT-EEG_HT | MAP - within expected range (+/- MAP_HT_REL % from usual MAP). HR - within the expected range (+/- HR_HT_REL %. | Decrease analgesic dosing and repeat INT_NOL_REPEAT min. until NOL < NOL_HT but not below MIN_ALG_DOSE. decreases hypnotic dosing and repeat until EEG_LT-EEG_HT | Confirms effectiveness of the OFA regimen (nociceptive stimulus not transmitted centrally) |
|  | Above NOL_HT | >EEG_HT following nociceptive stimuli | MAP increased following nociceptive stimuli but may be absent/delayed. | Increase analgesic dosing and repeat INT_NOL_REPEAT min. until NOL < NOL_HT but not above MAX_ALG_DOSE Increase hypnotic dosing | Interpreted as lack of effectiveness of the OFA regimen Ketamine, at high doses, |

TABLE 1-continued

| Clinical Concern | NOL | EEG | MAP & HR | Interventions (closed loop)- or pop up suggestion for intervention (open loop) | Recommendations & comments |
|---|---|---|---|---|---|
| | | | HR increased following nociceptive stimuli but may be absent/delayed | and repeat until EEG_LT-EEG_HT Send an alert to stop the nociception stimulus | increases the BIS values. |

Wherein:
NOL_HT = NOL High Threshold = 25 or another value defined in advance
NOL_XHT = NOL Extreme High Threshold = 50 or another value defined in advance
NOL_LT = NOL Low Threshold = 10 or another value defined in advance
NOL_min_time = NOL minimum time above threshold = 2 minutes or another value defined in advance
EEG_LT = 40 or another value defined in advance
EEG_HT = 60 or another value defined in advance
INT_NOL_REPEAT = 5 min or another value defined in advance
INT_MAP_REPEAT = 10 min or another value defined in advance
MAX_ALG_DOSE = Maximum analgesia dose - a predefined value (per minute) that even NOL is above NOL_HT, the machine won't provide more than this dose. This maximum value can be measure in "effect site concertation" values, or just as drip or bolus for a period of time.
MIN_ALG_DOSE = Min analgesia dose - a predefined value (per minute) that even NOL is below NOL_LT, the machine still provides. This minimum can be measure in "effect site concertation" values, or just as a drip or bolus for a period of time
MIN_ALG_DOSE_ WithRegional = a predefined value per minute, that might be even 0.
MAP_LT = Blood pressure low threshold = 60 mmHg or another value defined in advance.
MAP_HT = Blood pressure high threshold = 140 mmHg or another value defined in advance
MAP_HT_ REL = Blood pressure high threshold relative = 20% or another value defined in advance
HR_LT = Heart Rate low threshold = 45 BPM or another value defined in advance
HR_HT = Heart Rate high threshold = 90 BPM or another value defined in advance
HR_HT_REL = Heart Rate high threshold relative = 20% or another value defined in advance
Hypo_LT = Lower threshold of hypovolemia state
Ang_Step = a predefined value related to the medicine involved. - is configurable. Can be also an evolving number defined with Effective site concertation or bolus or drip The Emergence Phase:

According to some embodiments, the NOL trend will reflect the decreasing concentrations of hypnotics and opioids at the end of surgery in preparation of emergence from anesthesia, as the value during emergence from anesthesia will increase gradually in response to a reduction in analgesic/anesthetic doses/concentrations. Typically, the NOL value during emergence/tracheal extubation immediately increase to above 50.

Figure 3:
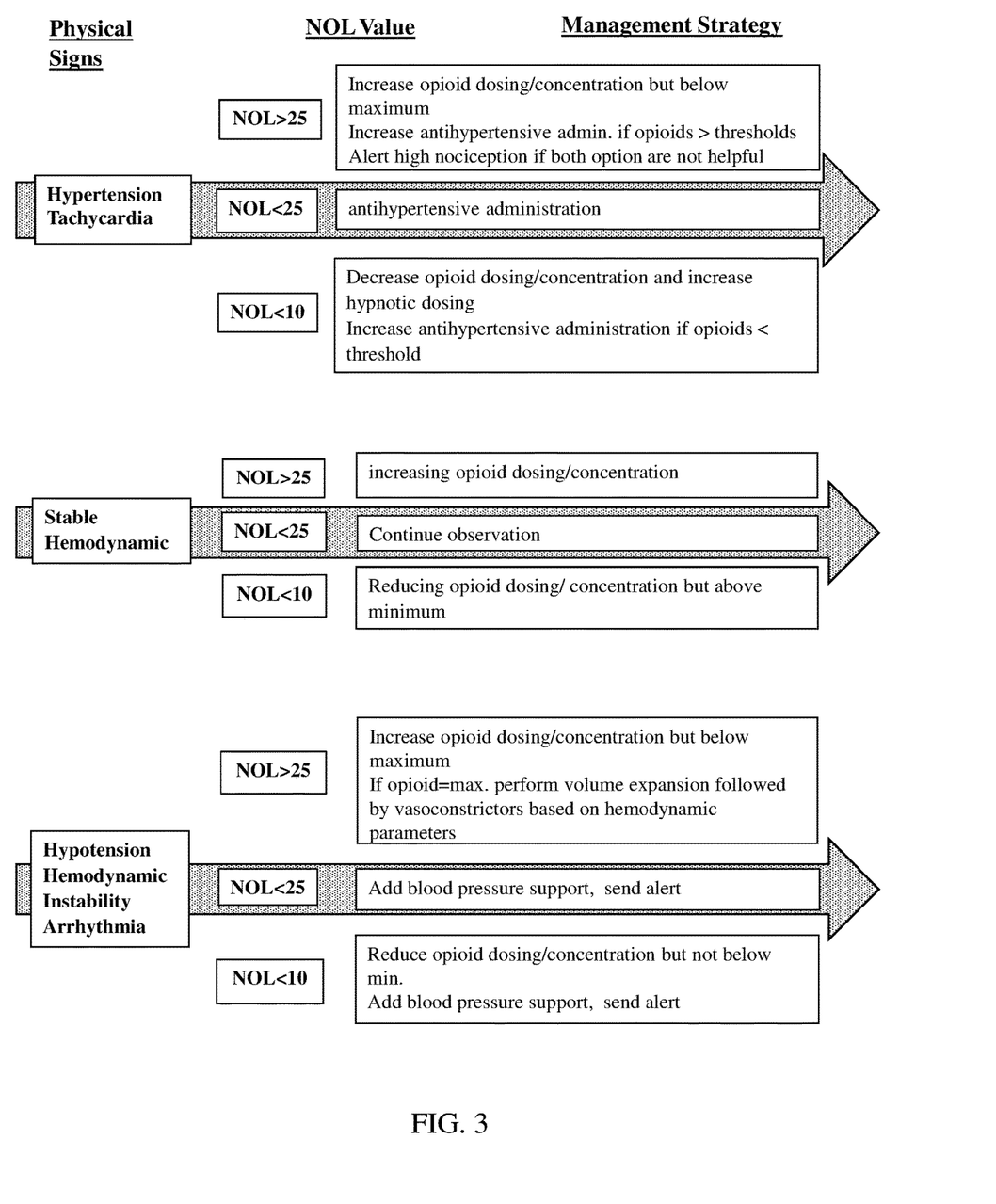
FIG. 3 illustratively depicts the herein disclosed perioperative nociception management decision algorithm, according to some embodiments.

According to some embodiments, the device, system and method disclosed herein may be configured for providing a treatment (optionally in closed loop) or a treatment recommendation (treatment assistance tool or "open-loop") based on the comparison of the nociception index value to the first and/or second threshold values and on a specific clinical concern as outlined in FIG. 3 and in table 1 above. It is understood that whenever a reference is done to a "close-loop" machine, an "open-loop" is likewise applicable.

According to some embodiments, the device, system and method disclosed herein may be configured to control operation of a medicament administration device, optionally in closed loop.

According to some embodiments, the medicament administration device may be an infusion pump, an implantable pump, an inhalation device.

According to some embodiments, the clinical concern may be a blood pressure related or a heart rate related clinical concern. According to some embodiments, the clinical concern is selected from hypertension, hypotension, tachycardia, hemodynamic instability, arrhythmia or any suitable combination thereof.

According to some embodiments, and as illustrated in FIG. 3, the device, system and method disclosed herein may, in the event of hypertension and/or tachycardia and a NOL above 25, optionally automatically adjust the medicament administration device to increase opioid concentration/dosing. According to some embodiments, if the opioids are administered at a predetermined maximum, the medicament administration device (same or different) may be instructed to increase the administration (or initiate administration) of an antihypertensive medicament. According to some embodiments, in case NOL levels remains unaltered, the device, system and method may be further configured to trigger an alert/alarm. According to some embodiments, in the event of hypertension and/or tachycardia and a NOL between 10 and 25, the device, system and method disclosed herein may, trigger the medicament administration device to administer an antihypertensive medicament. According to some embodiments, in the event of hypertension and/or tachycardia and a NOL below 10, the device, system and method disclosed herein may, trigger the medicament administration device to reduce the dosing/concentration of opioids and increase hypnotic dosing. Optionally, if the opioid concentration is below a predetermined threshold value, administration of an antihypertensive medicament may be increased (or initiated).

According to some embodiments, and as further illustrated in FIG. 3, the device, system and method disclosed herein may, in the event of stable hemodynamics and a NOL above 25, trigger the medicament administration device to increase opioid concentration/dosing. According to some embodiments, in the event of stable hemodynamics and a NOL between 10 and 25, the device, system and method disclosed herein may instruct the medicament administration device to maintain dosing protocol. According to some embodiments, in the event of stable hemodynamics and a NOL below 10, the device, system and method disclosed herein may trigger the medicament administration device to reduce the dosing/concentration of opioids (until reaching a predetermined minimum value).

According to some embodiments, and as illustrated in FIG. 3, the device, system and method disclosed herein may, in the event of hypotension, hemodynamic instability and/or arrhythmia and a NOL above 25, trigger the medicament administration device to increase opioid concentration/dosing. According to some embodiments, if the opioids are administered at a predetermined maximum, the medicament administration device (same or different) may be instructed to administrate vasoconstrictors. According to some embodiments, in the event of hypotension, hemodynamic instability and/or arrhythmia and a NOL between 10 and 25, the device, system and method disclosed herein may, blood pressure support and alarm/alert may be triggered. According to some embodiments, in the event of hypotension, hemodynamic instability and/or arrhythmia and a NOL below 10, the device, system and method disclosed herein may, trigger the medicament administration device to reduce the dosing/concentration of opioids and increase hypnotic dosing. Optionally, pressure support and an alarm/alert may be triggered.

It is understood that the increasing number of opioid users among the general population and the growing proportion of elderly, fragile and at-risk patients makes perioperative pain management challenging, for health care professionals. Advantageously, the herein disclosed device, system, method and incorporated algorithm enables an objective, effective and patient tailored perioperative pain management, by integrating nociception index values with clinical reasoning that bolster optimal nociception management.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this invention belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, a cloud based processing unit or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device comprising:
a processing unit configured to:
receive a plurality of nociception-related physiological parameters of an anesthetized patient from at least one physiological sensor of a first monitoring unit;
receive from an external monitor, an indication regarding a physiological signal related to a clinical concern, wherein the clinical concern is a mean arterial blood pressure above a predetermined upper threshold value (MAP_HT mmHg) measured for the patient; or a heart rate above a predetermined upper threshold value (HR-HT BPM) measured for the patient;
compute a nociception index value indicative of a level of nociception of the patient by applying a machine learning algorithm on the plurality of nociception-related physiological parameters and/or features derived therefrom; and
a) if the nociception index value exceeds a predetermined threshold value (NOL_HT) for a predetermined minimal amount of time (NOL_min_time min_HT), the processing unit issues a recommendation to increase analgesic dosing or triggers an operational command affecting a medicament administration device to increase the analgesic dosing;
b) if the nociception index value is below the NOL_HT but above a predetermined lower threshold value (NOL_LT), the processing unit issues a recommendation to administer a hypertensive agent or triggers an operational command affecting a medicament administration device to administer the anti-hypertensive agent; and c) if the nociception index value is below the NOL_LT for a predetermined minimal amount of time (NOL_min_time min_LT) and the analgesic dosing is above a minimal dosing (MIN_ALG_DOSE), the processing unit issues a recommendation to decrease analgesic dosing or triggers an operational command affecting a medicament administration device to decrease the analgesic dosing.

2. The device of claim 1, wherein the providing the control output further comprises providing to the medicament administration device a recommendation or a command to administer a anti-hypertensive agent if the mean arterial blood pressure remains about MAP_HT mmHg or above for a predetermined amount of time after the providing of the increased dose of the analgesic.

3. The device of claim 2, wherein if the nociception index value is between the first threshold value and the second threshold value for a predetermined amount of monitoring time, providing the control output comprises providing to the medicament administration device a recommendation or a command to administer a anti-hypertensive agent.

4. The device of claim 3, wherein the treatment further comprises increasing the dose of analgesic if the mean arterial blood pressure remains about MAP_HT mmHg for a predetermined amount of time after the providing the hypotensive agent.

5. The device of claim 1, wherein the at least physiological sensor comprise a Photoplethysmograph (PPG) or a Galvanic Skin Response (GSR) sensor and wherein the plurality of nociception-related physiological parameters comprise at least two physiological parameters selected from: pulse rate, pulse rate variability, pulse wave amplitude, skin conductance level, and skin conductance fluctuations.

6. The device of claim 1, wherein if a maximum analgesic dosing (MAX_ALG_DOSE) or a minimum analgesic dosing (MIN_ALG_DOSE) is reached, the processing unit is configured to issue an alert.

7. A device comprising:
a processing unit configured to:
receive a plurality of nociception-related physiological parameters of an anesthetized patient from at least one physiological sensor of a first monitoring unit;
receive from an external monitor an indication regarding a physiological signal related to a clinical concern, wherein the clinical concern is a mean arterial blood pressure at or below a predetermined lower threshold value (MAP_LT mmHg), a decrease in mean arterial blood pressure relative to a baseline mean arterial blood pressure (MAP_REL) of about 15% or more, or a heart rate at or below a predetermined low threshold value (HR_LT BPM);
compute a nociception index value indicative of a level of nociception of the patient by applying a machine learning algorithm on the plurality of nociception-related physiological parameters and/or features derived therefrom; and a. if the nociception index value exceeds a predetermined threshold value (NOL_HT) for a predetermined minimal amount of time (NOL_min_time min_HT), the processing unit issues a need to determine a hypovolemia value, if the hypovolemia value is below a lower threshold value, the processing unit issues a recommendation to increase rate of fluids to the patient and if the hypovolemia value is above an upper threshold value, the processing unit issues a recommendation to increase analgesic dosing or triggers an operational command affecting a medicament administration device to increase the analgesic dosing;

b. if the nociception index value is below the NOL_HT but above a predetermined lower threshold value (NOL_LT), the processing unit issues a recommendation to administer a sympathomimetic/adrenergic drug or triggers an operational command affecting a medicament administration device to administer the sympathomimetic/adrenergic drug; and c. if the nociception index value is below the NOL_LT and the analgesic dosing is above a minimal dosing (MIN_ALG_DOSE), the processing unit issues a recommendation to reduce analgesic dosing or triggers an operational command affecting a medicament administration device to decrease the analgesic dosing.

8. The device of claim 7, wherein when the nociception index value exceeds the first threshold value for a predetermined amount of monitoring time and an EEG of the patient is below a predetermined lower threshold value (EEG LT), or a burst suppression ratio is above 0, providing the control output comprises providing to the medicament administration device a recommendation or a command to reduce concentration of hypnotic agent and increase the dose of analgesic.

9. The device of claim 7, wherein if a minimal analgesic dosing (MIN_ALG_DOSE) is reached, the processing unit further issues a recommendation to administer a sympathomimetic/adrenergic drug or triggers an operational command affecting a medicament administration device to administer the sympathomimetic/adrenergic drug.

10. The device of claim 7, wherein if a maximum analgesic dosing (MAX_ALG_DOSE) or a minimum analgesic dosing (MIN_ALG_DOSE) is reached, the processing unit is configured to issue an alert.

11. The device of claim 7, wherein the at least physiological sensor comprise a Photoplethysmograph (PPG) or a Galvanic Skin Response (GSR) sensor and wherein the plurality of nociception-related physiological parameters comprise at least two physiological parameters selected from: pulse rate, pulse rate variability, pulse wave amplitude, skin conductance level, and skin conductance fluctuations.

* * * * *